United States Patent [19]
Fong et al.

[11] Patent Number: 5,496,859
[45] Date of Patent: Mar. 5, 1996

[54] GASIFICATION PROCESS COMBINED WITH STEAM METHANE REFORMING TO PRODUCE SYNGAS SUITABLE FOR METHANOL PRODUCTION

[75] Inventors: Wing-Chiu F. Fong, Yorktown Heights; Raymond F. Wilson, Fishkill, both of N.Y.

[73] Assignee: Texaco Inc., White Plains, N.Y.

[21] Appl. No.: 378,831

[22] Filed: Jan. 28, 1995

[51] Int. Cl.$^6$ .............................. C07C 27/06; C07C 31/04
[52] U.S. Cl. .......................... 518/703; 252/373; 518/702; 518/700
[58] Field of Search .................................. 518/700, 702, 518/703; 252/373

[56] References Cited

U.S. PATENT DOCUMENTS

| | | | |
|---|---|---|---|
| 4,888,130 | 12/1989 | Banguy | 252/373 |
| 4,910,228 | 3/1990 | Lywood | 518/703 |
| 4,927,857 | 5/1990 | MaShea, II | 518/703 |
| 5,252,609 | 10/1993 | Pinto | 518/703 |
| 5,312,843 | 5/1994 | Yamauch et al. | 518/702 |
| 5,431,855 | 7/1995 | Green et al. | 252/373 |

*Primary Examiner*—Werren B. Lone
*Attorney, Agent, or Firm*—Kenneth R. Priem; James L. Bailey; Richard A. Morgan

[57] ABSTRACT

An improved method for the production of stoichiometric ratioed syngas comprises partially oxidizing a gaseous feedstock containing substantial amounts of methane in a gasifier to produce a hot synthesis gas stream that is passed in indirect heat exchange through a steam reforming catalytic reactor. A portion of the steam reforming reaction products are mixed with the cooled gasifier synthesis gas stream exiting the steam reforming catalytic reactor to form a combined synthesis gas stream, called a "stoichiometric ratioed synthesis gas." The stoichiometric ratioed synthesis gas stream can then be passed into a methanol synthesis unit at substantially the specifications for optimal methanol production with little or no external compression. In a second embodiment the gasifier unit is arranged and operated in parallel with a primary steam reformer unit. The respective synthesis gas streams exiting each unit are combined to form a combined synthesis gas stream that undergoes oxidation in a secondary catalytic reformer unit to form a stoichiometric ratioed synthesis gas that requires minimal external compression before being converted to methanol.

16 Claims, 2 Drawing Sheets

GASIFICATION PROCESS COMBINED WITH STEAM METHANE REFORMING TO PRODUCE SYNGAS SUITABLE FOR METHANOL PRODUCTION

BACKGROUND OF THE INVENTION

1. Field of the Invention

This invention relates to an improved method for the production of a synthesis gas that is suitable for the production of methanol. The improved method integrates a gasification process with steam methane reforming.

2. Description of the Prior Art

Methanol is one of the major chemical raw materials, ranking third in volume behind ammonia and ethylene. Worldwide demand for methanol as a chemical raw material continues to rise especially in view of its increasingly important role as a source of alternative energy, for example, as a motor fuel additive or in the conversion of methanol to gasoline.

The significant reactions in methanol synthesis are based on the equilibrium reaction of carbon oxides (CO and $CO_2$) and hydrogen, in the direction of methanol formation as follows:

$$CO + 2H_2 \leftrightarrow CH_3OH \tag{1}$$

$$CO_2 + 3H_2 \leftrightarrow CH_3OH + H_2O \tag{2}$$

Reactions (1) and (2) are exothermic and proceed with volume contraction. Therefore, maximum methanol yields generally occur at low temperatures and high pressures.

An important way for producing methanol is by first producing a synthesis gas from a methane-containing gas, such as natural gas. The synthesis gas can be generated using steam methane reforming, partial oxidation or gasification, or a combined reforming or autothermal reforming process.

Steam methane reforming is the catalytic reaction of natural gas with steam to produce a synthesis gas or "syngas", which includes $H_2$, $CO_2$, CO, $CH_4$, and $H_2O$ with an $H_2$ to CO ratio of about 3:1 or higher. The steam methane reformation reaction is endothermic. Therefore, external heat is required. The natural gas and steam are typically fed into alloy tubes that contain a nickel based catalyst for the reforming reaction. The catalyst tubes are placed inside a refractory lined structure. A portion of the natural gas is used as fuel to provide the heat required for the reaction:

$$H_2O(g) + CH_4 \leftrightarrow 3H_2 + CO \tag{3}$$

The drawbacks of steam methane reforming include its limitation to low pressure applications on the order of about 100–400 psig. Steam methane reforming also produces a syngas with a high $CH_4$ impurity content in a range of about 3–15 percent, and requires the external supply of $CO_2$ for methanol syngas requirements.

Partial oxidation or gasification is a non-catalytic reaction of natural gas with oxygen under controlled oxygen conditions. The reaction is exothermic as shown in the following reaction:

$$CH_4 + \tfrac{1}{2}O_2 \rightarrow CO + 2H_2 \tag{4}$$

The partial oxidation process can be operated at high pressure to minimize or eliminate the syngas compression needed to reach the desired elevated pressure suitable for methanol production, typically about 200–2000 psig. However, the syngas produced from the partial oxidation process has a lower $H_2$:CO ratio with little or no $CH_4$ content. Typically, the $CH_4$ varies from about 0–0.5 percent, and the $H_2$:CO ratio varies from about 1.5–2.0. As a result, external $H_2$ would be needed to meet the methanol syngas requirements.

The combined reforming process uses a combination of conventional steam methane reforming, often referred to as "primary reforming", in combination with oxygenated catalytic reforming, often referred to as "secondary reforming", to generate stoichiometric ratioed synthesis gas for the production of methanol. See U.S. Pat. No. 4,888,130 to Banquy.

In a preferred aspect of the combined reforming process, a portion of the natural gas feedstock is fed to the primary reformer and the effluent is blended with the balance of the natural gas and oxygen prior to entering the secondary reformer. The drawback of the combined reforming process is that it is limited to moderate pressure applications, on the order of about 400 to 600 psig.

At higher pressures, reduced operating temperatures are necessary, and because increased amounts of $CH_4$ are present in the feed to the secondary reformer, it is more likely that soot or carbon formation will be increased. This can damage or deactivate the catalyst and lead to greater feed consumption to produce the required amount of carbon monoxide.

Most commercial methanol synthesis plants operate in a pressure range of about 700–2000 psig using various copper based catalyst systems depending on the technology used. A number of different state-of-the-art technologies are known for synthesizing methanol, and are commonly referred to as the ICI (Imperial Chemical Industries) process, the Lurgi process, and the Mitsubishi process.

The methanol syngas, also referred to as "stoichiometric ratioed synthesis gas", from the syngas generation unit is fed to a methanol synthesis reactor at the desired pressure of about 700 to 2000 psig, depending upon the process employed. The syngas then reacts with a copper based catalyst to form methanol. The reaction is exothermic. Therefore, heat removal is ordinarily required. The raw or impure methanol is then condensed and purified to remove impurities such as higher alcohols including ethanol, propanol, and the like. The uncondensed vapor phase comprising unreacted methanol syngas is recycled to the feed.

The operation of compressing the methanol synthesis gas requires expensive equipment that is costly to maintain. Moreover, the need to compress the methanol synthesis gas to reach suitable operating pressures for the methanol synthesis operation further increases the production cost of methanol. Therefore, a process that produces stoichiometric ratioed synthesis gas at elevated pressures without the need for external compression would be very attractive to the industry.

For optimal methanol production, the stoichiometric ratioed syngas supplied to the methanol synthesis unit generally conforms to the following specifications:

$$\frac{H_2 - CO_2}{CO + CO_2} \approx 1.9 – 2.1, \text{ and} \tag{1}$$

$$N_2, Ar \text{ and } CH_4 \leq 3.0\% \tag{2}$$

SUMMARY OF THE INVENTION

In accordance with the present invention, an improved method for the production of methanol comprises partially oxidizing a gaseous feedstock, typically natural gas containing substantial amounts of methane, to produce a hot pressurized gas stream. The hot gasifier synthesis gas stream, also referred to as "syngas" is passed in indirect heat exchange through a steam reforming catalytic reactor where an endothermic reforming reaction is conducted with a gaseous feedstock and steam.

The steam reforming reaction produces a reformer syngas. A portion of the reformer syngas is recycled to the gasifier feed and the remaining portion is combined with the partially cooled gasifier syngas exiting the catalytic reactor to form a stoichiometric ratioed synthesis gas. The ratio adjusted synthesis gas then enters the methanol synthesis unit at the conditions necessary to convert it to methanol with little or no external compression. Prior to entering the methanol synthesis unit, the ratio adjusted synthesis gas can be cooled to the desired operating temperature in a series of heat exchangers or steam generators or a combination of steam generators and heat exchangers for optimal heat recovery.

DESCRIPTION OF THE PREFERRED EMBODIMENTS

In accordance with the present invention, additional external compression of the methanol synthesis gas before it enters the methanol synthesis unit can be minimized or eliminated.

When additional external compression of the methanol synthesis gas is needed, it is generally on the order of about 100 to 1000 psi, preferably about 100 to 500 psi, and most preferably about 100 to 300 psi. Since the operating pressure of a methanol synthesis unit is generally on the order of about 700 to 2000 psig, the additional external compression needed to increase the pressure of the methanol synthesis gas to optimal operating pressure is considered minimal.

Another advantage of the present invention is that the need for a furnace to supply heat for the endothermic reaction that occurs in the catalytic steam reformer can be eliminated, resulting in the elimination of emissions of oxides of nitrogen, and carbon dioxide to the atmosphere.

There is also less consumption of gasifier feedgas as compared with current state-of-the-art gasifier syngas production technology. Better heat integration is achieved. Recycle loop compression power in the methanol synthesis unit is also reduced due to lower $CH_4$ content and the stoichiometric ratio of the methanol syngas supplied to the methanol synthesis reactor is optimal.

Figure 1:
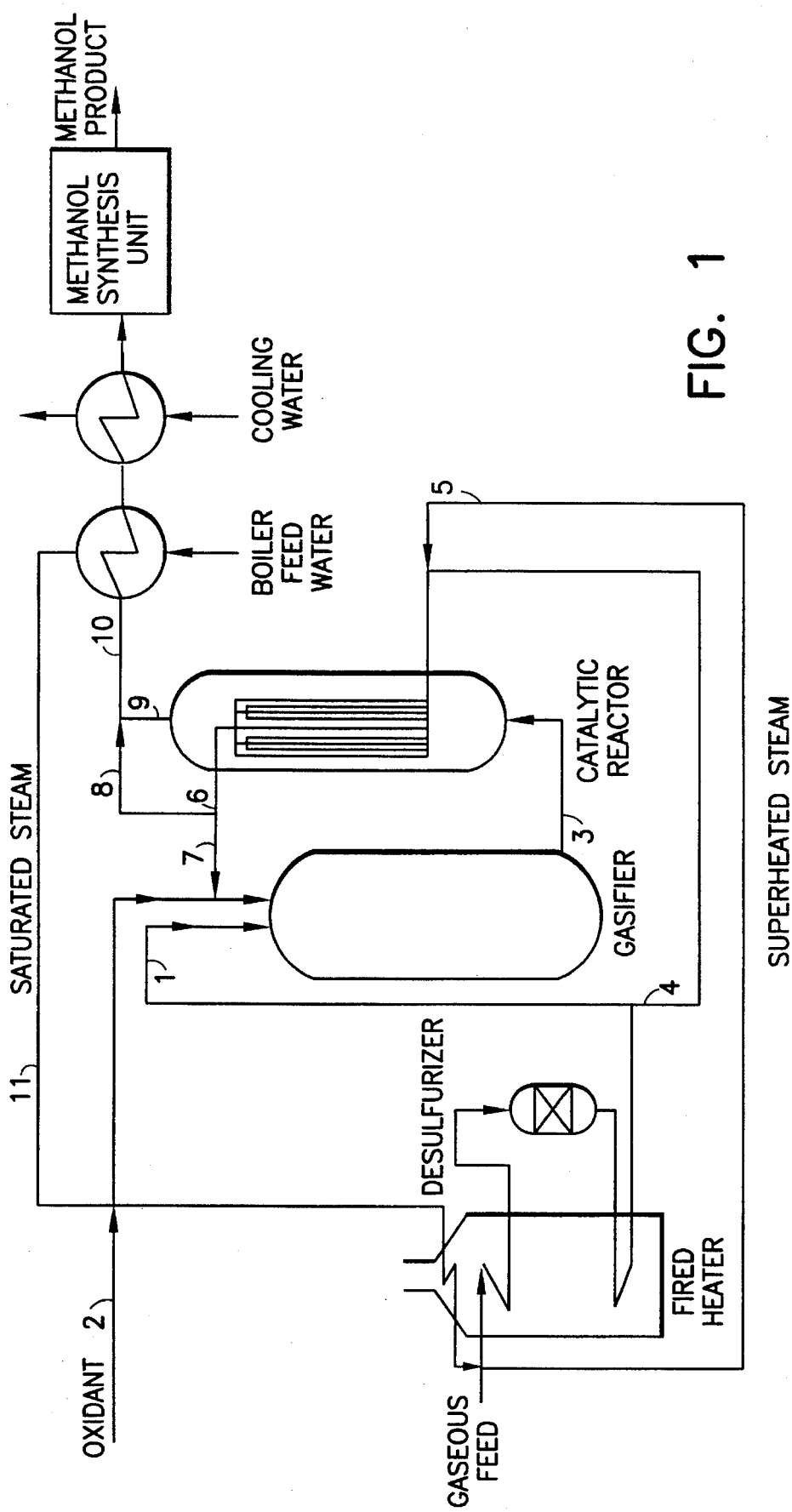
FIG. 1 is a schematic representation of the process wherein a portion of the reformer syngas exiting the catalytic reformer unit is combined with cooled gasifier syngas to form a stoichiometric ratioed combined syngas that needs little or no external compression to meet the methanol syngas specifications.

Referring to FIG. 1, a gaseous feedstock stream 1, containing substantial amounts of methane, such as natural gas or a refinery offgas is preheated in a fired heater to about 400°–500° F. and preferably desulfurized in a desulfurizing unit. Stream 1 can then be further preheated in the fired heater to about 500° to 1300° F., preferably about 800° to 1100° F. before being fed to a partial oxidation reactor, preferably a non-catalytic partial oxidation reactor.

The partial oxidation reactor is also referred to as a "partial oxidation gasifier", or simply a "gasifier", and these terms are used equivalently and interchangeably throughout the specification. The gasifiers that can be used in this invention are well known to those skilled in the art and are commonly referred to as "quench gasifiers" or "syngas cooler gasifiers".

An oxidant gas stream 2 is preferably preheated to a temperature above ambient to about 500° F., preferably about 200° to 300° F., and then fed to the gasifier. The oxidant gas stream 2 can be pure oxygen, oxygen enriched air, air, or any equivalent combination.

The partial oxidation reaction in the gasifier is an exothermic reaction conducted under conditions that are sufficient to convert gaseous feedstock stream 1 and oxidant gas stream 2 to a hot synthesis gas or "syngas" stream 3 that consists primarily of carbon monoxide and hydrogen. The gasifier unit operates at temperatures of about 2200°–2800° F., preferably about 2200°–2400° F. and a pressure of about 200–2000 psig, preferably about 600–1200 psig.

The hot syngas stream 3 exiting the gasifier has a temperature of about 2200°–2800° F., preferably about 2200°–2400° F. and a pressure of about 200–2000 psig, preferably about 600–1200 psig. The hot gasifier syngas stream 3 flows through a steam reforming catalytic reactor in indirect heat exchange with reactants undergoing a catalytic reformation reaction.

Preferably, the steam reforming catalytic reactor is constructed of shells and tubes, wherein the gasifier syngas passes through the shell and transfers heat to the tubes which contain a nickel-based catalyst for the endothermic steam reforming reaction.

The reactants entering the steam reforming catalytic reactor comprise a natural gas stream 4, preferably sulfur-free, and a steam stream 5. Steam stream 5 can be internally generated and superheated from a fired heater. The natural gas stream 4 can be supplied from a portion of the gaseous feedstock stream 1 that enters the gasifier.

The steam reforming catalytic reactor operates under endothermic conditions at a pressure of about 500–1200 psig and a temperature of about 1000°–1400° F. The reformation reaction produces a hydrogen-rich syngas stream 6 that can be partially recycled as stream 7 into the gasifier with the balance in stream 8 serving as a methanol syngas adjuster by being combined with partially cooled gasifier synthesis gas stream 9 that exits the catalytic reactor. Recycle stream 7 can vary from about 40–90 volume % of stream 6, preferably about 60–75 volume %. By difference, stream 8 can vary from about 10–60 volume %, preferably about 25–40 volume % of stream 6.

The combined syngas stream 10, also referred to as a "stoichiometric ratioed syngas", or a "methanol synthesis gas" stream, is formed from reformer syngas stream 8 and the partially cooled gasifier synthesis gas stream 9. Typically, combined syngas stream 10 exists at a temperature of about 1000° to 1400° F., and a pressure of about 200 to 2000 psig, preferably about 600 to 1200 psig. Combined syngas stream 10 can then be cooled by a series of indirect heat exchangers and/or steam generators to a temperature of about 100° to 600° F., preferably about 450° F. before entering a methanol synthesis unit to be converted into methanol. Preferably, stream 10 is cooled by at least one steam generator through which boiler feed water passes indirectly and exits as steam stream 11 at a temperature of about 500° to 640° F. The cooled combined methanol syngas stream 10 then enters the methanol synthesis unit at the conditions needed to convert it to methanol without external compression.

Steam stream 11 can then be passed into the fired heater to further superheat the steam prior to entering the steam reforming catalytic reactor as steam stream 5. In this way, heat recovery can be optimized.

In general, when the operating pressure of the steam methane reforming reaction increases, the wall thickness of the catalytic alloy reactor tubes must also be increased to accommodate the higher operating pressure, and the methane conversion decreases significantly because of the reduced heat transfer efficiency of the thicker alloy tube walls. Currently, the state-of-the-art catalytic alloy tubes used in steam methane reforming are operative up to about 400 psig. When the operating pressure rises above 400 psig, the methane conversion is significantly reduced and makes the process uneconomical.

The embodiment of the invention shown in FIG. 1 serves to alleviate the operating pressure limitation for the steam methane reforming reaction by placing the catalytic alloy reactor tubes, wherein the reforming reaction takes place, inside a high pressure vessel. This is in contrast to the atmospheric pressure furnace structure used in conventional steam methane reforming. In this manner, the maximum operating pressure inside the catalytic alloy tubes would be the sum of the high pressure vessel operating pressure plus up to about 400 psi operating pressure in the catalytic alloy tubes.

For example, where the high pressure vessel operating pressure is about 1000 psig, the operating pressure within the catalytic alloy reactor tubes can be up to about 1400 psig. If the operating pressure in the catalytic alloy reactor tubes that are placed inside the high pressure vessel is about 1100 psig and the high pressure vessel operating pressure is about 1000 psig, the pressure difference operating on the catalytic alloy tube wall is about 100 psi, which is significantly less than the maximum 400 psi operating limit. This enables relatively thinner walls to be used for the catalytic alloy tube reactor. The rate of heat transfer is more efficient when the walls of the catalytic alloy tubes are thinner. Thus, the embodiment shown in FIG. 1 can operate at higher pressures by not reducing methane conversion significantly. Methane conversion is still satisfactory, on the order of about 75 to 95 percent conversion at high pressure operation on the order of about 500 to 2500 psig.

Table 1 is a tabulation of the components and parameters for specific streams in FIG. 1.

TABLE 1

| | FIG. 1 Streams | | | | |
|---|---|---|---|---|---|
| Item | Natural Gas 1 | Oxidant 2 | Natural Gas 4 | Steam 5 | Combined Syngas 10 |
| Flow (1 bmole/hr) | 46.5 | 38.0 | 30 | 75 | 297.4 |
| Temp. (°F.) | 1100 | 300 | 1100 | 900 | 1350 |
| Pres. (psig) | 1075 | 1100 | 1075 | 1100 | 1000 |
| Component flow rate | | | | | |

TABLE 1-continued

| | FIG. 1 Streams | | | | |
|---|---|---|---|---|---|
| Item | Natural Gas 1 | Oxidant 2 | Natural Gas 4 | Steam 5 | Combined Syngas 10 |
| (1 bmole/hr) | | | | | |
| $H_2O$ | — | — | — | 75 | 65 |
| $CO_2$ | 0.46 | — | 0.30 | — | 12.3 |
| $CH_4$ | 44.64 | — | 28.80 | — | 2.2 |
| $C_2H_6$ | 0.70 | — | 0.45 | — | — |
| $C_3H_8$ | 0.23 | — | 0.15 | — | — |
| $N_2/Ar$ | 0.46 | 0.2 | 0.30 | — | 1.0 |
| CO | — | — | — | — | 61.6 |
| $H_2$ | — | — | — | — | 155.3 |
| $O_2$ | — | 37.8 | — | — | — |

As already noted, when the operating pressure of the steam methane reforming reaction increases, the wall thickness of the catalytic alloy reactor tubes must also be increased to accommodate the higher operating pressure, and the methane conversion decreases significantly because of the reduced heat transfer efficiency of the thicker alloy tube walls.

Figure 2:
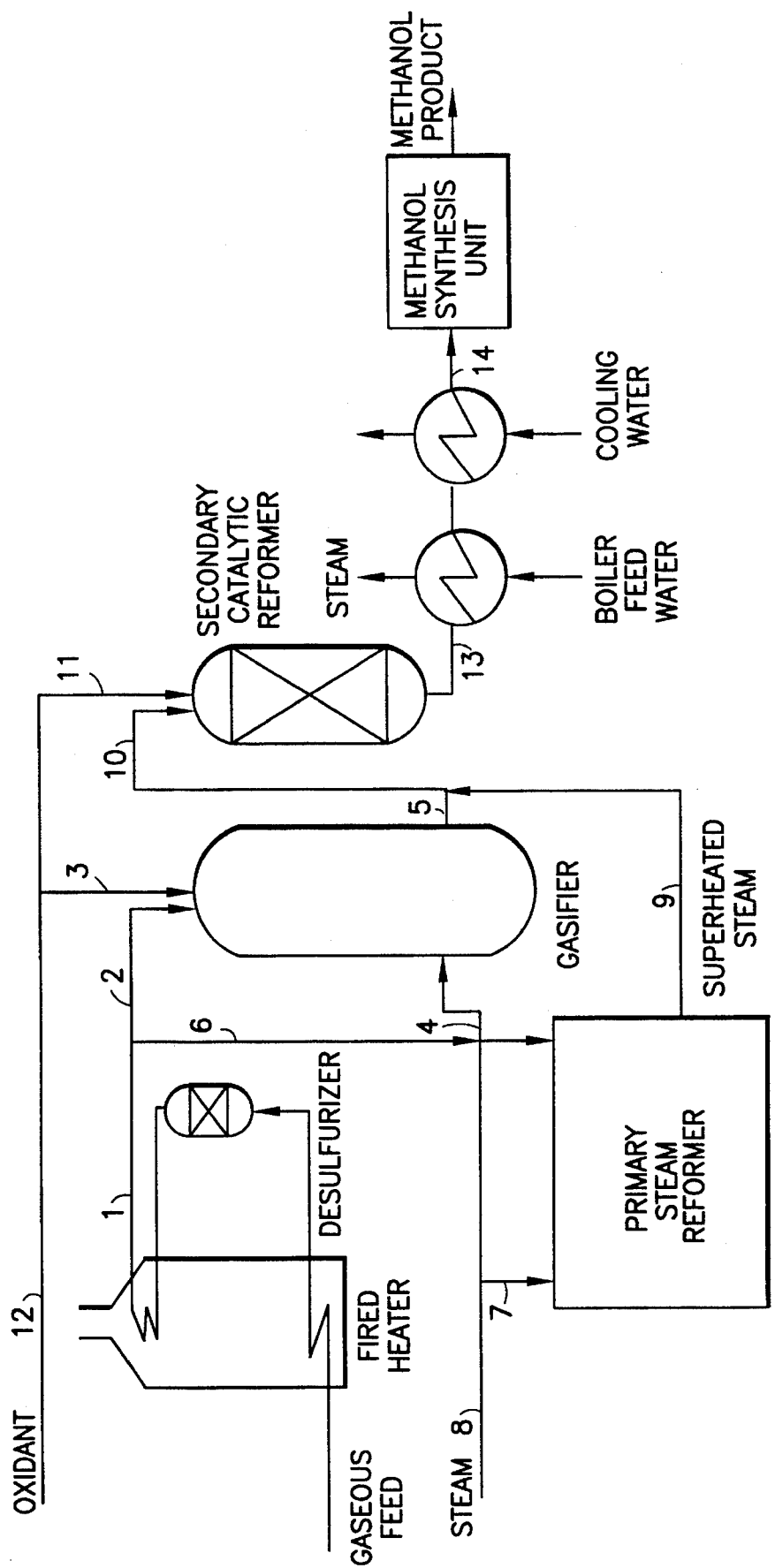
FIG. 2 is a schematic representation of the process wherein a gasifier and a primary steam reformer unit operate in parallel and wherein the effluents of each unit are combined and fed to a secondary reformer to produce a stoichiometric ratioed syngas that needs little or no external compression to meet the methanol syngas specifications.

The embodiment shown in FIG. 2 serves to alleviate the operating pressure limitations by integrating a non-catalytic gasification process with a secondary oxygenated catalytic reforming step so that the lower methane conversion due to higher operating pressure in primary steam methane reforming step is offset by a higher methane conversion (above 99 percent) in the gasification step followed by a smaller secondary reforming step acting as a controller to control methane content in the stoichiometric ratioed syngas stream prior to entering the methanol synthesis unit. This is in contrast to the process scheme described in U.S. Pat. No. 4,888,130 to Banquy.

The present invention will achieve higher methane conversion in the secondary reformer than U.S. Pat. No. 4,888,130 to Banquy due to lower methane content in the feed to the secondary reformer. This results in lower overall feed consumption due to the higher conversion of feedstocks. Therefore, smaller primary and secondary reforming units can be used. Furthermore, in the present invention, reduced amounts of methane in the feed gas stream to the secondary reformer will reduce the possibility of carbon formation.

Referring to FIG. 2, a non-catalytic gasifier unit and a primary steam reformer unit are arranged and operated in parallel with each unit being simultaneously supplied with a sulfur-free methane containing gas from stream 1 as a common source. Preferably, stream 1 can be natural gas. A portion of the sulfur-free methane containing natural gas stream 1 enters the gasifier as stream 2 with oxidant gas stream 3 and undergoes a partial oxidation reaction.

Steam stream 4 is also supplied to the gasifier to improve the $H_2/CO$ ratio and yield of hot synthesis gas stream 5 exiting the gasifier. Typically, the $H_2/CO$ ratio in gasifier syngas stream 5 without steam injection is about 1.75. An improved $H_2/CO$ ratio up to about 2.5 can be obtained by injecting steam into the gasifier.

At the same time that stream 2 enters the gasifier, the remaining portion of stream 1 enters the primary steam reformer as natural gas stream 6. A steam stream 7 also enters the primary reformer to react with natural gas stream 6. Preferably, steam in stream 8 serves as a common source of steam supply that is used to provide steam stream 4 to the gasifier and steam stream 7 to the primary reformer.

A hot H₂-rich primary reformer syngas stream 9 is produced from the primary steam reforming reaction of the natural gas stream 6 and steam stream 7 over a nickel-based catalyst. H₂-rich primary reformer syngas stream 9 exits the primary steam reformer and combines with the effluent hot syngas stream 5 exiting the gasifier to form a combined hot syngas stream 10 that enters a secondary catalytic reformer as a reactant and as a source of heat for the secondary reforming reaction. Stream 5 is about 30–60 volume percent, preferably 40–50 volume percent of stream 10.

An oxidant stream 11 also enters the secondary reformer as a reactant to promote partial oxidation of the combined hot syngas stream 10 over a nickel based catalyst at a temperature of about 1000°–2000° F. Preferably, a common source of oxidant in stream 12 is used to supply oxidant stream 11 to the secondary catalytic reformer and the oxidant stream 3 to the gasifier.

A secondary reforming syngas stream 13 exits the secondary reformer. As noted, this stream is also referred to as "stoichiometric ratioed syngas", or "methanol syngas", and substantially meets the methanol syngas specifications needed to produce methanol. The methanol syngas stream 13 can then be cooled to the required methanol synthesis temperature of about 100° to 600° F., preferably 300° to 500° F., prior to entering the methanol synthesis unit.

The temperature reduction of methanol synthesis gas stream 13 can be accomplished in a series of indirect heat exchangers and/or steam generators. The cooled methanol syngas stream 14 can then be fed to a methanol production unit with the need for only minimal external compression. Typically, the cooled methanol synthesis gas is at a pressure of about 500 to 1000 psig and requires little or no external compression. When additional compression is needed, it is generally on the order of about 100 to 500 psi depending upon the particular methanol synthesis process used. The parameters and components of specific streams in FIG. 2 are tabulated in Table 2.

What is claimed is:

1. An improved method for the production of methanol comprising:

(a) partially oxidizing a gaseous feedstock containing substantial amounts of methane in a gasifier to produce a hot gasifier synthesis gas stream containing substantial amounts of hydrogen and carbon monoxide;

(b) passing said hot gasifier synthesis gas stream through a steam reforming catalytic reactor in indirect heat exchange with reactants comprising a methane-containing gas and steam undergoing an endothermic catalytic steam reforming reaction in said catalytic reactor, to produce a reformer synthesis gas stream, and wherein the hot gasifier synthesis gas stream becomes cooled and exits the catalytic reactor as a cooled gasifier synthesis gas stream;

(c) combining said cooled gasifier synthesis gas stream with a portion of the reformer synthesis gas stream to form a stoichiometric ratioed synthesis gas stream, which is fed to a methanol synthesis unit to produce methanol, and wherein the stoichiometric ratioed synthesis gas requires little or no external compression to reach the optimal specifications necessary to produce methanol.

2. The method of claim 1 wherein the gaseous feedstock supplied to the gasifier is sulfur-free.

3. The method of claim 1 wherein the gaseous feedstock supplied to the steam reforming catalytic reactor is sulfur-free.

4. The method of claim 1, wherein the gaseous feedstock supplied to the gasifier and the gaseous feedstock supplied to the steam reforming catalytic reactor are sulfur-free and are supplied from a common source.

5. The method of claim 1, wherein the partial oxidation reaction occurring in the gasifier is conducted in the absence of a catalyst.

6. The method of claim 1, wherein the stoichiometric ratioed synthesis gas has the following specifications:

TABLE 2

| | FIG. 2 Streams | | | | | | |
|---|---|---|---|---|---|---|---|
| Item | Natural Gas 2 | Oxidant Feed 3 | Steam 4 | Natural Gas (bleedstream) 6 | Steam 7 | O₂ 11 | Cooled Combined Syngas 13 |
| Flow (1 bmole/hr) | 55 | 37 | 50 | 45 | 166.5 | 15 | 472.9 |
| Temp. (°F.) | 800 | 275 | 550 | 800 | 550 | 275 | 1700 |
| Pressure (psig) | 675 | 700 | 900 | 675 | 900 | 650 | 600 |
| Component flow rate | | | | | | | |
| (1 bmole/hr) | | | | | | | |
| H₂O | — | — | 50 | — | 166.5 | — | 128 |
| CO₂ | 0.55 | — | — | 0.45 | — | — | 28.1 |
| CH₄ | 52.8 | — | — | 43.2 | — | — | 2.0 |
| C₂H₆ | 0.83 | — | — | 0.68 | — | — | — |
| C₃H₈ | 0.28 | — | — | 0.22 | — | — | — |
| N₂ | 0.55 | — | — | 0.45 | — | — | 1.0 |
| CO | — | — | — | — | — | — | 69.4 |
| H₂ | — | — | — | — | — | — | 244.1 |
| O₂ | — | 36.8 | — | — | — | 14.9 | — |
| Ar | — | 0.2 | — | — | — | 0.1 | 0.3 |

$$\frac{H_2 - CO_2}{CO + CO_2} \approx 1.9\text{–}2.1; \text{ and} \quad (1)$$

$$N_2, Ar \text{ and } CH_4 \leq 3.0\%. \quad (2)$$

7. The method of claim 1, wherein a portion of the reformer synthesis gas exiting the catalytic reformer unit is recycled to the gasifier to control the $CH_4$ content to less than about 3.0%.

8. The method of claim 1, wherein the combined synthesis gas stream is cooled before being converted to methanol.

9. The method of claim 1, wherein the steam reforming catalytic reactor can be operated at pressures of up to about 2000 psig.

10. An improved method for the production of methanol comprising:

(a) arranging and operating a gasifier unit and a primary steam reformer unit in parallel with each of said units being simultaneously supplied with a gaseous feedstock comprising a methane containing gas stream and steam, wherein the gasifier unit produces a hot synthesis gas stream containing substantial amounts of hydrogen and carbon monoxide, and wherein the primary steam reformer unit produces a primary reformer syngas stream;

(b) combining the gasifier synthesis gas stream and the primary reformer synthesis gas stream to form a combined hot synthesis gas stream;

(c) passing said combined hot synthesis gas stream into a secondary catalytic reformer unit wherein said combined synthesis gas stream undergoes reaction with an oxidant stream to form a stoichiometric ratioed synthesis gas, which is fed to a methanol synthesis unit to produce methanol.

11. The method of claim 10, wherein the stoichiometric ratioed synthesis gas needs minimal external compression prior to entering the methanol synthesis unit at the optimal specifications for producing methanol.

12. The method of claim 10, wherein the stoichiometric ratioed synthesis gas is cooled prior to entering the methanol synthesis unit.

13. The method of claim 10, wherein the stoichiometric ratioed synthesis gas has the following specifications:

$$\frac{H_2 - CO_2}{CO + CO_2} \approx 1.9\text{--}2.1; \text{ and} \quad (1)$$

$$N_2, Ar \text{ and } CH_4 \leq 3.0\%. \quad (2)$$

14. The method of claim 10, wherein an oxidant gas is supplied to the gasifier unit in a first stream from a common source that provides oxidant gas in a second stream to the secondary catalytic reformer unit.

15. The method of claim 10, wherein the methane containing gas supplied to the gasifier unit comes from a common source that also supplies the methane containing gas to the primary steam reformer unit.

16. The method of claim 8, wherein the primary steam reformer unit can be operated at a pressure of up to about 1000 psig.

* * * * *